United States Patent
Cai et al.

(10) Patent No.: US 6,448,246 B1
(45) Date of Patent: Sep. 10, 2002

(54) SUBSTITUTED 4H-1,4-BENZOTHIAZINE-2-CARBOXAMIDE: GABA BRAIN RECEPTOR LIGANDS

(75) Inventors: Guolin Cai, Guilford, CT (US); Gang Liu, Agoura, CA (US); Pamela A. Albaugh, Clinton, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/578,928

(22) Filed: May 25, 2000

Related U.S. Application Data

(60) Provisional application No. 60/136,015, filed on May 25, 1999.

(51) Int. Cl.[7] .................... C07D 279/16; C07D 417/12; A61K 31/5415
(52) U.S. Cl. .................. 514/224.2; 544/51; 544/52
(58) Field of Search .................. 514/224.2; 544/51, 544/52

(56) References Cited

FOREIGN PATENT DOCUMENTS

| DE | 3229125 | | 2/1984 |
|---|---|---|---|
| EP | 174458 | * | 3/1986 |
| WO | WO 99/10347 | | 3/1999 |

OTHER PUBLICATIONS

Barnard et al., "International Union of Pharmacology. XV. Subtypes of . gamma. –aminobutyric acidA receptors: Classifiction on the basis of subunit structure and receptor function" *Pharmacological Reviews,* vol. 50 No. 2, Jun. (1998), pp. 291–313–314.

Balbi et al., J. Heterocyl. Chem. (1996), 33 (2) 347–350.

Cecchetti et al., J. Heterocycl. Chem. (1992), 29 (2), 375–382.

Liso et al. J. Heterocycl. Chem. (1980), 17 (4), 793–796.

Montiel et al., PubMed Abstract (Neural Plast. 7(1–2): 1–8, 2000).*

Acri et al., PubMed Abstract (Neuroscience, 77(2): 371–8, Mar. 1997).*

Layzer, Degenerative Diseases of the Nervous System, Cecil Textbook of Medicine, 20th Edition, vol. 2, pp. 2050–2057, 1996.*

* cited by examiner

*Primary Examiner*—Deepak R. Rao
(74) *Attorney, Agent, or Firm*—McDonnell Boehnen Hulbert & Berghoff

(57) ABSTRACT

Disclosed are 4H-1,4-Benzothiazine-2-carboxamides. These compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, depression, sleep, cognitive and seizure disorders, and overdose with benzodiazepine drugs and for enhancement of alertness. Pharmaceutical compositions, including packaged pharmaceutical compositions, are further provided. Compounds of the invention are also useful as probes for the localization of GABAA receptors in tissue samples.

46 Claims, No Drawings

SUBSTITUTED 4H-1,4-BENZOTHIAZINE-2-CARBOXAMIDE: GABA BRAIN RECEPTOR LIGANDS

This invention claims priority to U.S. Provisional Application No. 60/136,015, filed May 25, 1999, which is hereby incorporated by reference in its entirety.

FIELD OF THE INVENTION

This invention relates to 4H-1,4-Benzothiazine-2-carboxamides and more specifically to such compounds that bind with high selectivity and high affinity to the benzodiazepine site of $GABA_A$ receptors. This invention also relates to pharmaceutical compositions comprising such compounds and to the use of such compounds in treatment of certain central nervous system (CNS) diseases. This invention also relates to the use of these 4H-1,4-Benzothiazine-2-carboxamide compounds in combination with one or more other CNS agents to potentiate the effects of the other CNS agents. Additionally this invention relates to the use such compounds as probes for the localization of $GABA_A$ receptors in tissue sections.

DESCRIPTION OF THE RELATED ART

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg Science 1989; 245:1389–1392 and Knight et. al., Recept. Channels 1998; 6:1–18). Evidence such as message distribution, genome localization and biochemical study results suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$ (Mohler et. al. Neuroch. Res. 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., cooper, et al., The Biochemical Basis of Neuropharmacology, $6^{th}$ ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of certain other CNS active compounds. For example, there is evidence that selective serotonin reuptake inhibitors (SSRIs) may show greater antidepressant activity when when used in combination with $GABA_A$ selective ligands than when used alone.

Various 1,4-benzothiaxine-2-carboxamide 1,1-dioxides have been disclosed. See, e.g. J. Heterocycl. Chem. (1996), 33 (2), 347–350. German Patent No. DE 3229125 also disloses 4-oxo-1,4-benzothiazine-2-carboxylate compounds which are used as animal growth substances, antiinfective agents, and preservatives. Furthermore, J. Heterocycl. Chem. (1992), 29 (2), 375–382 discloses 6-fluoro-4-oxo-1,4-benzothiazine-2-carboxcylic acid compounds said to mimic antibacterial quinolones. J. Heterocycl. Chem. (1980), 17 (4), 793–796 describes the synthesis of 1,4-benzothiazines.

SUMMARY OF THE INVENTION

Disclosed are 4H-1,4-Benzothiazine-2-carboxamides that bind to cell surface receptors, preferably GABA receptors. The compounds of the invention possess affinity for the benzodiazepine site of $GABA_A$ receptors, including human $GABA_A$ receptors. Preferred compounds of the invention exhibit high selectivity to the benzodiazepine site of the $GABA_A$ receptor. These compounds are therefore useful in the treatment of a broad array of diseases and/or disorders in patients which are characterized by modulation of $GABA_A$ receptors.

Such diseases and disorders include, but are not limited to depression, anxiety, sleep disorders, cognitive disorders, low alertness, psychosis, obesity, pain, Parkinson's disease, Alzheimer's disease, neurodegenerative diseases, movement disorders, Down's syndrome, and benzodiazepine overdoses.

Thus, the invention provides compounds of Formula I (shown below), and pharmaceutical compositions comprising compounds of Formula I.

The invention further comprises methods of treating patients suffering from certain CNS disorders with an effective amount of a compound of the invention. The patient may be a human or other mammal. Treatment of humans, domesticated companion animals (pets) or livestock animals suffering from certain CNS disorders with an effective amount of a compound of the invention is encompassed by the invention.

In a separate aspect, the invention provides methods of potentiating the actions of other CNS active compounds. These methods comprise administering an effective amount of a compound of the invention with another CNS active compound.

Additionally this invention relates to the use of the compounds of the invention as probes for the localization of $GABA_A$ receptors in tissue sections.

Accordingly, a broad aspect of the invention is directed to compounds of Formula I:

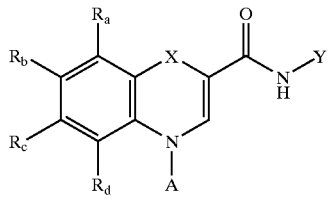

I or the pharmaceutically acceptable non-toxic salts thereof wherein:

A is hydrogen, alkyl, alkenyl, alkynyl, aminoalkyl, or mono- or dialkylamino;

X is S, S=O, or O=S=O;

$R_a$, $R_b$, $R_c$, and $R_d$, independently represent
  i) hydrogen, halogen, hydroxy, amino, nitro, cyano, thio, haloalkyl, or
  ii) lower alkyl, alkenyl, alkynyl, mono- or dialkylamino, $C_0$–$C_6$alkyl-S—$C_0$–$C_6$alkyl, $C_0$–$C_6$alkyl-SH, $C_0C_0$–$C_6$alkyl-SO—$C_1$–$C_6$alkyl, $C_0$–$C_6$alkyl-SO$_2$—$C_0$–$C_6$alkyl, $C_0$–$C_6$alkyl-SO$_2$H, alkoxy, or $C_3$–$C_7$ cycloalkyl, each of which is optionally substituted on an alkyl portion with —OR$_1$ or —NR$_2$R$_3$; and is lower alkyl, cycloalkyl, or cycloalkyl(alkyl) aryl, arylalkyl, heteroaryl, or heteroarylalkyl, each of which is optionally substituted with
  i) halogen, hydroxy, amino, nitro, cyano, thio, haloalkyl, $C_0$–$C_6$alkyl-SO—$C_1$–$C_6$alkyl, $C_0$–$C_6$alkyl-SO$_2$—$C_0$–$C_6$alkyl, $C_0$–$C_6$alkyl-SO$_2$H; or
  ii) lower alkyl, alkenyl, alkynyl, —OR$_1$, —NR$_2$R$_3$, SR$_4$, each of which is optionally substituted with halogen, hydroxy, lower alkyl, lower alkoxy, amino, thio, mono- or di($C_1$–$C_6$)alkylamino, —ZR$_1$, —O—G$_1$—OR$_1$;

where

Z is O, S, or NH;

G$_1$ is lower alkyl or cycloalkyl;

R$_1$ is hydrogen, lower alkyl or $C_3$–$C_7$ cycloalkyl, where each alkyl is optionally substituted with lower alkoxy, $C_3$–$C_7$ cycloalkoxy, or mono- or di($C_1$–$C_6$) alkylamino;

R$_2$ and R$_3$ are the same or different and represent hydrogen, lower alkyl, $C_3$–$C_7$ cycloalkyl; or R$_2$ and R$_3$ together with the nitrogen atom to which they are attached form a 5- or 6-membered heterocyclic ring; and R$_4$ is hydrogen, or lower alkyl or $C_3$–$C_7$ cycloalkyl, where each alkyl is optionally substituted with lower alkoxy, $C_3$–$C_7$ cycloalkoxy or mono- or di($C_1$–$C_6$) alkylamino.

DETAILED DESCRIPTION OF THE INVENTION

The invention also includes compounds of Formula Ia:

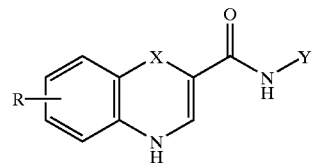

Ia or the pharmaceutically acceptable non-toxic salts thereof wherein:

X is S, S=O, or O=S=O;

R represents up to 4 groups independently chosen from
  i) hydrogen, halogen, hydroxy, amino,
  ii) lower alkyl, $C_3$–$C_7$ cycloalkyl, lower alkyl, alkenyl, alkynyl, mono- or dialkylamino, each of which is optionally substituted with —OR$_1$ or —NR$_2$R$_3$;

Y is lower alkyl, cycloalkyl, or cycloalkyl(alkyl) aryl, arylalkyl, heteroaryl, or heteroarylalkyl, each of which is optionally substituted with
  i) halogen, hydroxy, amino, haloalkyl, thio,
  ii) lower alkyl, alkenyl, alkynyl,—OR$_1$, —NR$_2$R$_3$, SR$_4$, each of which is optionally substituted with halogen, hydroxy, lower alkyl, lower alkoxy, amino, thio;

where

R$_1$ is hydrogen, lower alkyl or $C_3$–$C_7$ cycloalkyl, where each alkyl is optionally substituted with lower alkoxy, $C_3$–$C_7$ cycloalkoxy, or mono- or di($C_1$–$C_6$) alkylamino;

R$_2$ and R$_3$ are the same or different and represent hydrogen, lower alkyl, $C_3$–$C_7$ cycloalkyl; or R$_2$ and R$_3$ together with the nitrogen atom to which they are attached form a 5- or 6-membered heterocyclic ring; and R$_4$ is hydrogen, or lower alkyl or $C_3$–$C_7$ cycloalkyl, where each alkyl is optionally substituted with lower alkoxy, $C_3$–$C_7$ cycloalkoxy, or mono- or di($C_1$–$C_6$)alkylamino.

In Formula I above, Y can also represent G$_1$, where G$_1$ is a lower alkyl group or a $C_3$–$C_7$ cycloalkyl group such as, for example, cyclohexyl. Further, Y may represent —G$_1$—ZR$_1$, where G$_1$ is as defined above, R$_1$ is as defined above in Formula I, and Z is O, S or NH. Y may also represent —G$_1$—NR$_2$R$_3$ where G$_1$ is as defined above and R$_2$ and R$_3$ are as defined above in Formula I.

Similarly, the Y group in Formula I above can also represent a heterocyclic group such as, for example, piperidinyl or tetrahydrofuranyl.

Further, Y can also represent —G$_1$—W, where G$_1$ is as defined above and W is —O—G$_1$—OR$_1$, where R$_1$ is as defined in Formula I. W may also be (un)substituted aryl or (un)substituted-arylalkyl, such as, for example, 4-methoxyphenyl or 4-methoxybenzyl. W may also be un) substituted heteroaryl or (un) substituted heteroarylalkyl, such as 4-pyridyl, 2-thiazolyl, or 2-furanyl. W may further represent (un)substituted-heterocycloalkyl groups such as, for example, 1,2-methylenedioxybenzene.

Preferred compounds of Formula I are those where G$_1$ are methyl, ethyl or propyl and W is phenyl mono- or disubstituted independently with halogen, alkoxy, alkyl, thiol, heteroarylalkyl, or mono- or disubstituted-aminoalkyl.

In addition, the present invention encompasses compounds of Formula II:

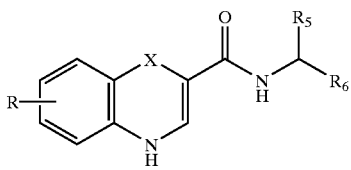

wherein X and R are as defined above for Formula I and R₅ and R₆ are the same or different and represent
  (i) hydrogen;
  (ii) lower alkyl optionally substituted with halogen, —OR₁, —NR₂R₃, SR₄ where R₁, R₂, R₃, and R₄ are as defined above in Formula I; or aryl or heteroaryl, each of which is mono-, di- or trisubstituted independently with halogen, hydroxyl, lower alkyl, lower alkoxy, amino, thiol, or mono- or dialkylamino where each alkyl portion is lower alkyl; or
  (iii) aryl or heteroaryl mono-, di- trisubstituted independently with halogen, hydroxyl, lower alkyl, lower alkoxy, amino, thiol, or mono- or dialkylamino where each alkyl portion is lower alkyl; or
  R₅ and R₆ together with the carbon atom to which they are attached form a 5, 6, or 7 membered carbocyclic ring.

Preferred compounds of Formula II are where R is hydrogen, R₅ is hydrogen and R₆ is lower alkyl optionally substituted with lower alkoxy, or R₆ is aryl or heteroaryl mono- or disubstituted with lower alkoxy, lower alkyl, halogen, mono- or dialkylamino, or thiol.

A preferred group of compounds of the invention is encompassed by Formula III:

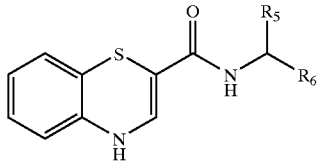

wherein R₅ and R₆ are as defined above for Formula II.

More preferred compounds of Formula III are where R₅ is hydrogen and R₆ is lower alkyl or optionally substituted aryl, preferably optionally substituted phenyl.

Other preferred compounds of the invention are encompassed by Formula IV.

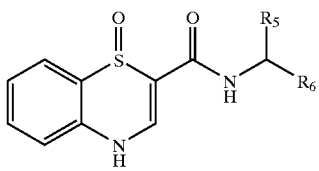

wherein R₅ and R₆ are as defined above for Formula II.

More preferred compounds of Formula IV are where R₅ is hydrogen and R₆ is lower alkyl, or aryl or heteroaryl mono-, di- or trisubstituted independently with halogen, hydroxyl, lower alkyl, lower alkoxy, amino, thiol, or mono- or dialkylamino.

Even more preferred compounds of Formula IV are where R₆ is phenyl mono- or disubstituted with methoxy, ethoxy, bromo, chloro, fluoro, methyl, dialkylamino or thiol, or where R₆ is furanyl, thiazolyl, imidazolyl, or pyridyl.

Still other preferred compounds of the invention are encompassed by Formula V.

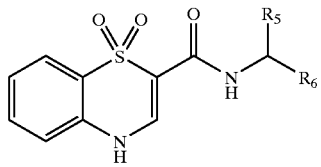

wherein R₅ and R₆ are defined as above for Formula II.

More preferred compounds of Formula V are where R₅ is hydrogen and R₆ is lower alkyl substituted with lower alkoxy, or aryl or heteroaryl mono-, di- or trisubstituted independently with halogen, hydroxyl, lower alkyl, lower alkoxy, amino, thiol, or mono- or dialkylamino.

Even more preferred compounds of Formula V are where R₆ is phenyl mono- or disubstituted with methoxy, bromo, chloro, methyl, dialkylamino, or thiol, or where R₆ is furanyl, thiazolyl, imidazolyl, or pyridyl.

Yet other preferred compounds of the invention are represented by Formula VI.

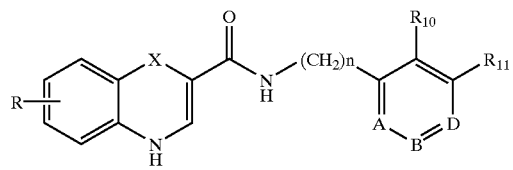

wherein R and X are as defined above for Formula I; n is 1–6; A, B and D are the same or different and represent N or CR₁₂, provided that at least two of A, B and D are CR₁₂; and R₁₀, R₁₁, R₁₂ are independently selected at each occurrence from hydrogen, halogen, hydroxy, lower alkyl, lower alkoxy, amino, thiol, or mono- or dialkylamino where each alkyl portion is independently lower alkyl, provided that at least two of R₁₀, R₁₁, and R₁₂ are hydrogen.

More preferred compounds of Formula VI, include those of Formula VIa

Formula VIa

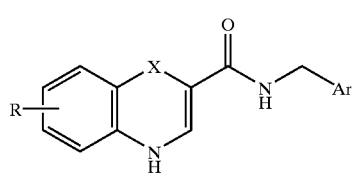

or the pharmaceutically acceptable non-toxic salts thereof wherein:
  X is S, S=O, or O=S=O;
  R represents up to 4 groups independently selected from hydrogen, halogen, hydroxy, amine, nitro, cyano, thio, haloalkyl, lower alkyl, alkenyl, alkynyl, mono- or dialkylamino, or alkoxy; and
  Ar is phenyl or pyridyl each of which is optionally mono-, di-, or trisubstituted with halogen, hydroxy, amine, haloalkyl, thio, lower alkyl, alkenyl, alkynyl, alkoxy, or mono or dialkylamino.

Other preferred compounds of Formula VIa are those where R represents only hydrogen, and Ar is phenyl optionally mono-, di-, or trisubstituted with halogen, hydroxy, amine, haloalkyl, thio, lower alkyl, alkenyl, alkynyl, alkoxy, or mono or dialkylamino.

Also preferred are compounds of Formula VII

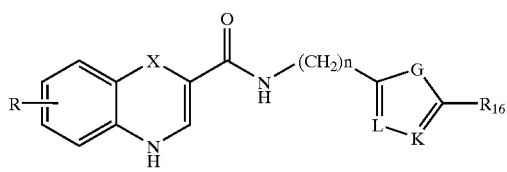

wherein R and X are as defined above for Formula I; n is 1–6; G is NH, S or O; L and K are the same or different and represent N or $CR_{17}$, provided that if G is O, then L and K are both $CR_{17}$; and $R_{16}$ and $R_{17}$ are independently selected at each occurrence from hydrogen, halogen, hydroxy, lower alkyl, lower alkoxy, amino, thiol, and mono- or dialkylamino where each alkyl portion is independently lower alkyl.

More preferred compounds of Formula VII are where R is hydrogen, n is 1, and $R_{16}$ and $R_{17}$ are hydrogen when L or K are $CR_{17}$.

When any variable occurs more than one time in any constituent or formula for a compound, its definition at each occurrence is independent of its definition at every other occurrence. Thus, for example, if a group is shown to be substituted with 0–2 R*, then said group is optionally substituted with up to two R* groups and the definition of each of the substituients R* is independent of the definition of every other R*. Also, combinations of substituents and/or variables are permissible only if such combinations result in stable compounds.

In certain situations, compounds of Formula I may contain one or more asymmetric carbon atoms, so that the compounds can exist in different stereoisomeric forms. These compounds can be, for example, racemates or optically active forms. In these situations, the single enantiomers, i. e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid and base addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitic, bencoic, citric, tartaric, maleic, hydroiodic, alkanoic such as acetic, HOOC—$(CH_2)_n$—$A_c$OOH where n is 0–4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

The present invention also encompasses the acylated prodrugs of the compounds of Formula I. Those skilled in the are will recognize various synthetic methodologies which may be employed to prepare non-toxic pharmaceutically acceptable addition salts and acylated prodrugs of the compounds encompassed by Formula I.

By "alkyl" or "lower alkyl" in the present invention is meant straight or branched chain alkyl groups having 1 to about 6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "$C_x$–$C_y$ alkyl" is meant an alkyl group as defined above having the indicated number of carbon atoms, where $C_0$ alkyl indicates that no alkyl group is present.

By "alkoxy and "lower alkoxyl" and "$C_1$–$C_6$ alkoxy" in the present invention is meant straight or branched chain alkoxy groups having 1 to about 6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

"Alkenyl" is intended to include hydrocarbon chains of either a straight or branched configuration and one or more unsaturated carbon-carbon bonds which may occur in any stable point along the chain, such as ethenyl and propenyl.

"Alkynyl" is intended to include hydrocarbon chains of either a straight or branched configuration and one or more triple carbon-carbon bonds which may occur in any stable point along the chain, such as ethynyl and propynyl.

By the terms "dialkylamino" and "di($C_1$–$C_6$)alkylamino" as used herein is meant amino groups substituted with two alkyl groups, i.e., $C_{1-C6}$ alkyl groups, that are the same or different.

The term "haloalkyl" as it is used herein includes both branched and straight-chain saturated aliphatic hydrocarbon groups having the specified number of carbon atoms, substituted with 1 or more halogens (for example —$C_vF_w$ where v=1 to 3 and w=1 to (2v+1). Examples of haloalkyl include, but are not limited to, 2-bromoethyl, trifluoromethyl, trichloromethyl, pentafluoroethyl, and pentachloroethyl.

By the term "halogen" in the present invention is meant fluorine, bromine, chlorine, and iodine.

By "cycloalkyl", e.g., $C_3$–$C_7$ cycloalkyl, in the present invention is meant cycloalkyl groups having 3 to about 7 atoms such as, for example cyclopropyl, cyclobutyl, cyclopenyl, cyclohexyl, and cycloheptyl.

By "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridinyl, pyrimidinyl, (iso)quinolinyl, napthyridinyl, benzimidazolyl, benzoxazolyl.

By "heteroarylalkyl" is meant a heteroaryl group as described above joined at the indicated point of attachment via an alkyl group of about 1 to about 3 carbon atoms.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. A preferred aryl is phenyl.

By "arylalkyl" is meant an aryl group as described above joined at the indicated point of attachment via an alkyl group of about 1 to about 3 carbon atoms.

Representative compounds of the invention are shown below in Table 1.

TABLE 1

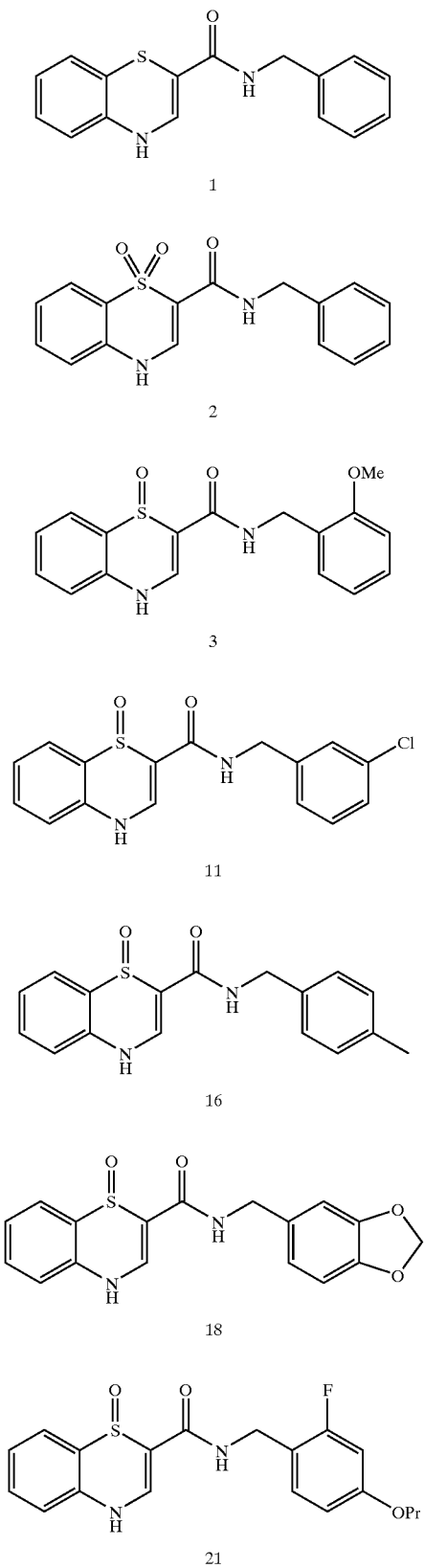

TABLE 1-continued

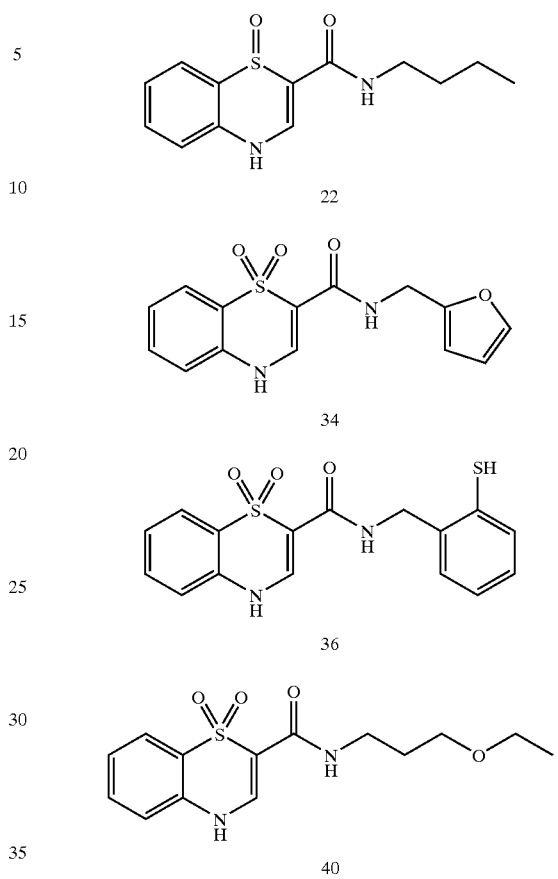

The substituted 1,4-benzothiazine-2-carboxamide derivatives of the invention interact with a GABA binding site, the benzodiazepine (BDZ) receptor, as demonstrated in the examples. Without wishing to be bound to any particular theory it is believed that this interaction results in the pharmaceutical utility of the compounds.

The compounds of Formula I and their salts are suitable for the diagnosis and treatment of anxiety, depression, memory impairment, Alzheimer's dementia, Down Syndrome, sleep, cognitive and seizure disorders, and overdose with benzodiazepine drugs and for enhancement of alertness, both in human and non-human animals including companion animals, e.g. domestic pets, especially dogs and cats and livestock animals, e.g. sheep, swine and cattle.

The diseases and/or disorders that can be treated using compound and compositions according to the invention include:

Depression, e.g. depression, atypical depression, bipolar disorder, depressed phase of bipolar disorder.

Anxiety, e.g. general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

This invention relates to benzothiazine-2-carboxamide derivatives that bind with high affinity to the benzodiazepine site of $GABA_A$ receptors, including human $GABA_A$ receptors. This invention also includes such compounds that bind with high selectivity to the benzodiazepine site of $GABA_A$ receptors, including human $GABA_A$ receptors.

The invention also provides pharmaceutical compositions comprising compounds of the invention.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. 5-$HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl) methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The present invention also pertains to methods of inhibiting the binding of benzodiazepine compounds, such as Ro15-1788, to the $GABA_A$ receptors which methods involve contacting a compound of the invention with cells expressing $GABA_A$ receptors, wherein the compound is present at a concentration sufficient to inhibit benzodiazepine binding to $GABA_A$ receptors in vitro. This method includes inhibiting the binding of benzodiazepine compounds to $GABA_A$ receptors in vivo, e.g., in a patient given an amount of a compound of Formula I that would be sufficient to inhibit the binding of benzodiazepine compounds to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via an $GABA_A$ receptor binding assay, such as the assay described in Example 9. The $GABA_A$ receptors used to determine in vitro binding may be obtained from a variety of sources, for example from preparations of rat cortex or from cells expressing cloned human $GABA_A$ receptors.

The present invention also pertains to methods for altering the signal-transducing activity, particulary the chloride ion conductanc of $GABA_A$ receptors, said method comprising exposing cells expressing such receptors to an effective amount of a compound of the invention. This method includes altering the signal-transducing activity of $GABA_A$ receptor s in vivo, e.g., in a patient given an amount of a compound of Formula I that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 10.

The $GABA_A$ receptor ligands provided by this invention and labeled derivatives thereof are also useful as standards and reagents in determining the ability of a potential pharmaceutical to bind to the $GABA_A$ receptor.

Labeled derivatives the $GABA_A$ receptor ligands provided by this invention are also useful as radiotracers for positron emission tomography (PET) imaging or for single photon emission computerized tomography (SPECT).

Non-toxic pharmaceutically acceptable salts include, but are not limited to salts with inorganic acids such as hydrochloride, sulfate, phosphate, diphosphate, hydrobromide, and nitrite or salts with an organic acid such as malate, maleate, fumarate, tartrate, succinate, citrate, acetate, lactate, methanesulfonate, p-toluenesulfonate, 2-hydroxyethylsulfonate, salicylate and stearate. Similarly, pharmaceutically acceptable cations include, but are not limited to sodium, potassium, calcium, aluminum, lithium and ammonium. The present invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention have pharmacological properties that include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Various assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

General methods suitable for the preparation of compounds of the present invention are given in Schemes I–III.

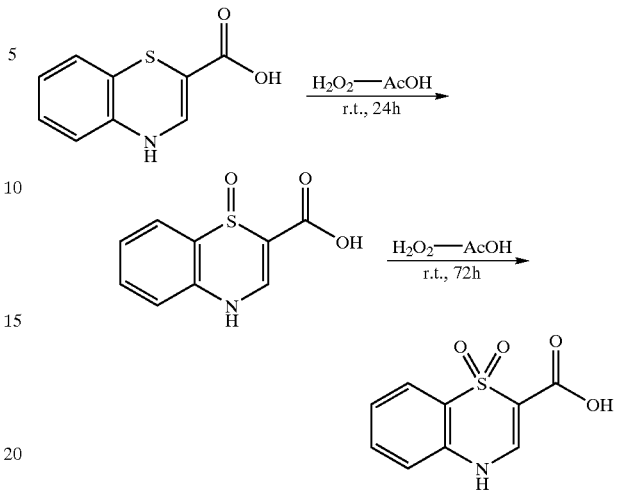

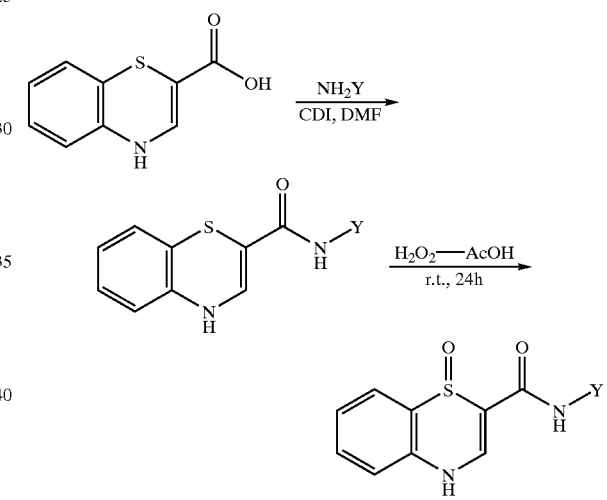

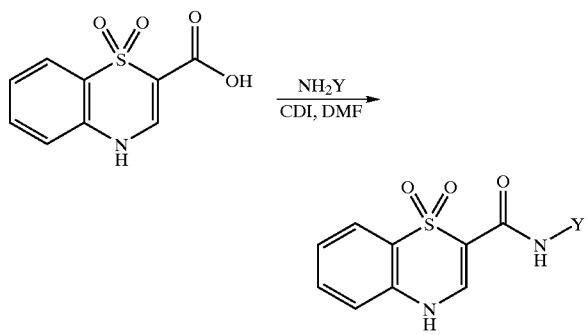

In Scheme I, the substituent Y carries the definition set forth above for Formula I.

Those having skill in the art will recognize that the starting materials and reaction conditions may be varied and additional steps employed to produce compounds encompassed by the present inventions, as demonstrated by the following examples.

As shown in Scheme I, an appropriate 1,4-benzothiazine-2-carboxylic acid is oxidized with, for example, hydrogen peroxide in acetic acid, to afford the desired sulfoxide. The sulfoxide is then further oxidized to the corresponding 1,1-dioxide-1,4-benzothiazine-2-carboxylic acid, which is subsequently coupled to an appropriate amine in the presence of a standard peptide coupling reagent, such as, for example, 1,1'-carbonyldiimidazole (CDI) as shown in Scheme III. Scheme II shows a similar coupling reaction with the starting 1,4-benzothiazine-2-carboxylic acid. The resulting 1,4-benzothiazine-2-carboxamide is then oxidized to the sulfoxide.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates as well as any necessary reagents may be obtained from commercial sources, prepared from commercially available organic and/or inorganic sources, or prepared using well known synthetic methods.

Representative examples of methods for preparing intermediates of the invention are set forth below.

EXAMPLE 1

1—Oxo-1,4-benzothiazine-2-carboxylic Acid

A suspension of 1,4-benzothiazine-2-carboxlic acid (0.9 g, 4.1 mmol) in hydrogen peroxide (30%, 15 mL) and acetic acid ( 5 mL) is stirred at room temperature for 20 h. The solid is filtered and washed with water to give 1-oxide-1,4-benzothiazine-2-carboxylic acid (0.85 g, 87% yield) as a white-greyish solid, m.p. 203–205° C.

EXAMPLE 2

1,1-Dioxo-1,4-benzothiazine-2-carboxylic Acid

A suspension of 1-oxide-1,4-benzothiazine-2-carboxlic acid (0.85 g, 4.1 mmol) in hydrogen peroxide (30%, 15 mL) and acetic acid ( 10 mL) is stirred at room temperature for 48 h. The solid is filtered and washed with water to give 1-oxide-1,4-benzothiazine-2-carboxylic acid (0.78 g, 85% yield) as a white solid, m.p. 229–231° C.

EXAMPLE 3

N-Benzyl-1,4-benzothiazine-2-carboxamide

A solution of 1,4-benzothiazine-2-carboxlic acid (70 mg, 0.36 mmol) and 1,1'-carbonyldiimidazole (70 mg, 0.43 mmole) in DMF ( 5 mL) is stirred at 80° C. for 30 mins. It is then treated with benzylamine (0.05 mL, 0.43 mmol) and heated at 80° C. for 1 h. The reaction mixture is cooled to room temperature, taken up with ethylacetate, and extracted with water (3×10 mL). The organic layer is dried over sodium sulfate and concentrated. The solid is filtered and washed with ethylacetate to give N-benzyl-1,4-benzothiazine-2-carboxamide (35 mg, 35% yield) as a white solid (compound 1), m.p. 160–162° C.

EXAMPLE 4

N-Benzyl-1,1-dioxide-1,4-benzothiazine-2-carboxamide

A solution of 1,1-dioxide-1,4-benzothiazine-2-carboxlic acid (50 mg, 0.22 mmol) and 1,1'-carbonyldiimidazole (51 mg, 0.32 mmole) in DMF ( 5 mL) is stirred at 80° C. oil-bath for 30 mins. It is then treated with benzylamine (0.04 mL, 0.36 mmol) and heated at 80° C. for 1 h. The reaction solution is cooled to room temperature, taken up with EtAc, and extracted with water (3×10 mL). The organic layer is dried over sodium sulfate and concentrated. The solid is filtered and washed with ethylacetate to give N-benzyl-1,1-dioxide-1,4-benzothiazine-2-carboxamide (30 mg, 44% yield) as a white solid (compound 2), m.p. 188–191° C.

EXAMPLE 5

N-2-Methoxybenzyl-,1-oxide-1,4-benzothiazine-2-carboxamide

A solution of N-2-methoxybenzyl-1,4-benzothiazine-2-carboxamide (200 mg, 0.64 mmol) ) in hydrogen peroxide (30%, 15 mL) and acetic acid ( 5 mL) is stirred at room temperature for 20 h. The solid is filtered and washed with ethylacetate to give N-2-methoxybenzyl-1-oxide-1,4-benzothiazine-2-carboxamide (170 mg, 81% yield) as a white solid (compound 3), m.p. 210–211° C.

EXAMPLE 6

The following compounds are prepared essentially according to the procedures described in Examples 1–6:

a) N-Benzyl-1-oxide-1,4-benzothiazine-2-carboxamide (compound 4), m.p.229 –230° C.

b) N-3-Methoxybenzyl-1-oxide-1,4-benzothiazine-2-carboxamide (compound 5), m.p. 198–200° C.

c) N-4-Methoxybenzyl-1-oxide-1,4-benzothiazine-2-carboxamide (compound 6), m.p. 218–219° C.

d) N-2-Ethoxybenzyl-1-oxide-1,4-benzothiazine-2-carboxamide (compound 7), m.p. >210° C.

e) N-3-Ethoxybenzyl-1-oxide-1,4-benzothiazine-2-carboxamide (compound 8), m.p. >250° C.

f) N-4-Ethoxybenzyl-1-oxide-1,4-benzothiazine-2-carboxamide (compound 9), m.p. >360° C.

g) N-2-Chlorobenzyl-1-oxide-1,4-benzothiazine-2-carboxamide (compound 10), m.p. 235–238° C.

h) N-3-Chlorobenzyl-1-oxide-1,4-benzothiazine-2-carboxamide (compound 11), m.p. 208–210° C.

i) N-4-Chlorobenzyl-1-oxide-1,4-benzothiazine-2-carboxamide (compound 12), m.p. 230–232° C.

j) N-2-Fluorobenzyl-1-oxide-1,4-benzothiazine-2-carboxamide (compound 13), m.p. 218–219° C.

k) N-3-Fluorobenzyl-1-oxide-1,4-benzothiazine-2-carboxamide (compound 14), m.p. 204–205° C.

l) N-4-Fluorobenzyl-1-oxide-1,4-benzothiazine-2-carboxamide (compound 15), m.p. 203–205° C.

m) N-4-Methylbenzyl-1-oxide-1,4-benzothiazine-2-carboxamide (compound 16), m.p. >300° C.

n) N-α-Methylbenzyl-1-oxide-1,4-benzothiazine-2-carboxamide (compound 17), m.p. 220–222° C.

o) N-3,4-Methylenedioxybenzyl-1-oxide-1,4-benzothiazine-2-carboxamide (compound 18), m.p. 210–212° C.

p) N-3,4-Dimethoxybenzyl-1-oxide-1,4-benzothiazine-2-carboxamide (compound 19), m.p. 210–211° C.

q) N-2-Fluoro-4-methoxylbenzyl-1-oxide-1,4-benzothiazine-2-carboxamide (compound 20), m.p. 218–219° C.

r) N-2-Fluoro-4-propoxybenzyl-1-oxide-1,4-benzothiazine-2-carboxamide (compound 21), m.p. 205–206° C.

s) N-n-Butyl-1-oxide-1,4-benzothiazine-2-carboxamide (compound 22), m.p. 218–220° C.

t) N-2-Thiophenylmethyl-1-oxide-1,4-benzothiazine-2-carboxamide (compound 23), m.p. 218–219° C.

u) N-3-Thiophenylmethyl-1-oxide-1,4-benzothiazine-2-carboxamide (compound 24), m.p. 211–213° C.

v) N-2-Furanylmethyl-1-oxide-1,4-benzothiazine-2-carboxamide (compound 25), m.p. 210–212° C.

w) N-4-Picolyl-1-oxide-1,4-benzothiazine-2-carboxamide (compound 26), m.p. >140° C.

x) N-2-Chlorobenzyl-1,1-dioxide-1,4-benzothiazine-2-carboxamide (compound 27), m.p. 218–220° C.

y) N-3-Chlorobenzyl-1,1-dioxide-1,4-benzothiazine-2-carboxamide (compound 28), m.p. 120–124° C.

z) N-2-Bromobenzyl-1,1-dioxide-1,4-benzothiazine-2-carboxamide (compound 29), m.p. 198–200° C.

aa) N-2-Methoxybenzyl-1,1-dioxide-1,4-benzothiazine-2-carboxamide (compound 31), m.p. 150–151° C.

bb) N-3,4-Dimethoxybenzyl-1,1-dioxide-1,4-benzothiazine-2-carboxamide (compound 32), m.p. 177–178° C.

cc) N-2,3-Dimethoxybenzyl-1,1-dioxide-1,4-benzothiazine-2-carboxamide (compound 33), m.p. 127–129° C.

dd) N-2-Furanylmethyl-1,1-dioxide-1,4-benzothiazine-2-carboxamide (compound 34), m.p. 164–165° C.

ee) N-2-Thiazolylmethyl-1,1-dioxide-1,4-benzothiazine-2-carboxamide (compound 35), m.p. 185–186° C.

ff) N-2-Thiophenylmethyl-1,1-dioxide-1,4-benzothiazine-2-carboxamide (compound 36), m.p. 198–200° C.

gg) N-3-Dimethylaminomethylbenzyl-1,1-dioxide-1,4-benzothiazine-2-carboxamide hydrochloride (compound 37), m.p. >290° C.

hh) N-4-Methylaminomethylbenzyl-1,1-dioxide-1,4-benzothiazine-2-carboxamide hydrochloride (compound 38), m.p. >290° C.

ii) N-4-Imidazolylmethylbenzyl-1,1-dioxide-1,4-benzothiazine-2-carboxamide hydrochloride (compound 39), m.p. 238–240° C.

jj) N-3-Ethoxypropyl-1,1-dioxide-1,4-benzothiazine-2-carboxamide hydrochloride (compound 40).

EXAMPLE 7

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 8

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

EXAMPLE 9

Binding Assay

The following assay is a standard assay of $GABA_A$ receptor binding. The high affinity and high selectivity of compounds of this invention for the benzodiazepine site of the $GABA_A$ receptor is shown using the binding assay described in Thomas and Tallman (J. Bio. Chem. 1981; 156:9838–9842, and J. Neurosci. 1983; 3:433–440). Essentially the same assay is described below.

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations containi 100 μl of tissue homogenate, 100 μl of radioligand, (0.5 mM $^{3}H$-Ro15-1788 [$^{3}H$-Flumazenil], specific activity 80 Ci/mmol), and test compound or control (see below), and are brought to a total volume of 500 μl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}H$ Ro15-1788 with 10 μM Diazepam (Research Biochemicals International, Natick, Mass.). Data were collected in triplicate, averaged, and percent inhibition of total specific binding (Total Specific Binding=Total—Nonspecific) was calculated for each compound.

A competition binding curve is obtained with up to 11 points spanning the compound concentration range from $10^{-12}M$ to $10^{-5}M$ obtained per curve by the method described above for determining percent inhibition. $K_i$ values are calculated according the Cheng-Prussof equation. When tested in this assay compounds of the invention exihibit $K_i$ values of less than 1 μM, preferred compounds of the invention have $K_i$ values of less than 500 nM and more preferred compounds of the invention have $K_i$ values of less than 100 nM.

EXAMPLE 10

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. Xenopus Laevis oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\beta_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM–9 μM). Each oocyte is exposed to increasing concentrations of compound in order to evaluate a concentration/effect relationship. Compound efficacy is calculated as a percent-change in current amplitude: 100*((Ic/I)-1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM Ro15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula:

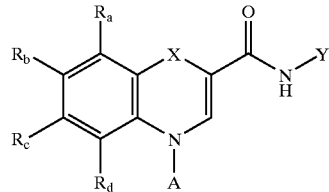

or a pharmaceutically acceptable non-toxic salt thereof wherein:
A is hydrogen, alkyl, alkenyl, alkynyl, aminoalkyl, or mono- or dialkylamino;
X is S=O, or O=S=O;
$R_a$, $R_b$, $R_c$, and $R_d$, independently represent
  i) hydrogen, halogen, hydroxy, amino, nitro, cyano, —SH, haloalkyl, or
  ii) lower alkyl, alkenyl, alkynyl, mono- or dialkylamino, $C_0$–$C_6$alkyl-S—$C_1$–$C_6$alkyl, $C_1$–$C_6$alkyl-SH, $C_0$–$C_6$alkyl-SO—$C_1$–$C_6$alkyl, $C_0$–$C_6$alkyl-SO$_2$—$C_1$–$C_6$alkyl, $C_0$–$C_6$alkyl-SO$_2$H, alkoxy, or $C_3$–$C_7$ cycloalkyl, each of which is optionally substituted with —$OR_1$ or —$NR_2R_3$; and
Y is lower alkyl, cycloalkyl, or aryl substituted with a cycloalkylalkyl group, arylalkyl, heteroaryl, or heteroarylalkyl, each of which is optionally substituted with
  i) halogen, hydroxy, amino, nitro, cyano, —SH, haloalkyl, $C_0$–$C_6$alkyl-SO—$C_1$–$C_6$alkyl, $C_0$–$C_6$alkyl-SO$_2$—$C_1$–$C_6$alkyl, $C_0$–$C_6$ alkyl-SO$_2$H; or
  ii) lower alkyl, alkenyl, alkynyl, —$OR_1$, —$NR_2R_3$, $SR_4$, each of which is optionally substituted with halogen, hydroxy, lower alkyl, lower alkoxy, amino, —SH, mono- or di($C_1$–$C_6$) alkylamino, —$ZR_1$, or —O—$G_1$—$OR_1$;
where
  Z is O, S, or NH;
  $G_1$ is lower alkyl or cycloalkyl;
  $R_1$ is hydrogen, lower alkyl or $C_3$–$C_7$ cycloalkyl, where each alkyl is optionally substituted with lower alkoxy, $C_3$–$C_7$ cycloalkoxy, or mono- or di($C_1$–$C_6$) alkylamino;
  $R_2$ and $R_3$ are the same or different and represent hydrogen, lower alkyl, $C_3$–$C_7$ cycloalkyl; or
  $R_2$ and $R_3$ together with the nitrogen atom to which they are attached form a 5- or 6-membered heterocyclic ring; and
  $R_4$ is hydrogen, or lower alkyl or $C_3$–$C_7$ cycloalkyl, where each alkyl is optionally substituted with lower alkoxy, $C_3$–$C_7$ cycloalkoxy, or mono- or di($C_1$–$C_6$) alkylamino.
2. A compound of the formula:

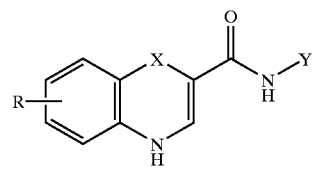

or a pharmaceutically acceptable non-toxic salt thereof wherein:

X is S=O, or O=S=O;
R represents up to 4 groups independently chosen from
  i) hydrogen, halogen, hydroxy, amino,
  ii) lower alkyl, $C_3$–$C_7$ cycloalkyl, lower alkoxy, alkenyl, alkynyl, mono- or dialkylamino, each of which is optionally substituted with —$OR_1$ or —$NR_2R_3$;
Y is lower alkyl, cycloalkyl, or aryl substituted with a cycloalkylalkyl group, arylalkyl, heteroaryl, or heteroarylalkyl, each of which is optionally substituted with
  i) halogen, hydroxy, amino, haloalkyl, —SH,
  ii) lower alkyl, alkenyl, alkynyl, —$OR_,$, —$NR_2R_3$, $SR_4$, each of which is optionally substituted with halogen, hydroxy, lower alkyl, lower alkoxy, amino, mono- or dialkylamino, or —SH;
  where
    $R_2$ and $R_3$ are the same or different and represent hydrogen, lower alkyl, $C_3$–$C_7$ cycloalkyl; or
    $R_2$ and $R_3$ together with the nitrogen atom to which they are attached form a 5- or 6-membered heterocyclic ring; and
    $R_4$ is hydrogen, or lower alkyl or $C_3$–$C_7$ cycloalkyl, where each alkyl is optionally substituted with lower alkoxy, $C_3$–$C_7$ cycloalkoxy, or mono- or di($C_1$–$C_6$) alkylamino.

3. A compound of the formula:

or a pharmaceutically acceptable non-toxic salt thereof wherein:
X is S=O, or O=S=O;
R is hydrogen, halogen, or lower alkyl or cycloalkyl optionally substituted independently with —$OR_1$, or —$NR_2R_3$; and
$R_5$ and $R_6$ are the same or different and represent hydrogen; lower alkyl optionally substituted with halogen, —$OR_1$, —$NR_2R_3$, or $SR_4$; or lower alkyl optionally substituted with aryl or heteroaryl mono-, di- or trisubstituted independently with halogen, hydroxyl, lower alkyl, lower alkoxy, amino, thiol, or mono- or dialkylamino where each alkyl portion is lower alkyl;
$R_1$ is hydrogen, or lower alkyl or $C_3$–$C_7$ cycloalkyl, where each alkyl is optionally substituted independently with lower alkoxy or mono- or dialkylamino where each alkyl portion is lower alkyl;
$R_2$ and $R_3$ are the same or different and represent hydrogen, lower alkyl, cycloalkyl; or
$R_2$ and $R_3$ together with the nitrogen atom to which they are attached form a heterocyclic moiety;
$R_4$ is hydrogen, or lower alkyl or cycloalkyl optionally substituted independently with lower alkoxy or mono- or dialkylamino where each alkyl portion is lower alkyl; or
$R_5$ and $R_6$ are the same or different and represent aryl or heteroaryl mono-, di- or trisubstituted independently with halogen, hydroxyl, lower alkyl, lower alkoxy, amino, thiol, or mono- or dialkylamino where each alkyl portion is lower alkyl; or
$R_5$ and $R_6$ together with the carbon atom to which they are attached form a 5, 6, or 7 membered carbocyclic ring.

4. A compound according to claim 3 which is:

or a pharmaceutically acceptable non-toxic salt thereof wherein:
$R_5$ and $R_6$ are the same or different and represent hydrogen; lower alkyl optionally substituted with halogen, —$OR_1$, —$NR_2R_3$, $SR_4$; or lower alkyl optionally substituted with aryl or heteroaryl mono-, di- or trisubstituted independently with halogen, hydroxyl, lower alkyl, lower alkoxy, amino, thiol, or mono- or dialkylamino where each alkyl portion is lower alkyl; where
$R_1$ is hydrogen, or lower alkyl or cycloalkyl optionally substituted independently with lower alkoxy or mono- or dialkylamino where each alkyl portion is lower alkyl;
$R_2$ and $R_3$ are the same or different and represent hydrogen, lower alkyl, cycloalkyl; or
$R_2$ and $R_3$ together with the nitrogen atom to which they are attached form a heterocyclic moiety;
$R_4$ is hydrogen, or lower alkyl or cycloalkyl optionally substituted indpendently with lower alkoxy or mono- or dialkylamino where each alkyl portion is lower alkyl; or
$R_5$ and $R_6$ are the same or different and represent aryl or heteroaryl mono-, di- or trisubstituted independently with halogen, hydroxyl, lower alkyl, lower alkoxy, amino, thiol, or mono- or dialkylamino where each alkyl portion is lower alkyl; or
$R_5$ and $R_6$ together with the carbon atom to which they are attached form a 5, 6, or 7 membered carbocyclic ring.

5. A compound according to claim 3 which is:

or a pharmaceutically acceptable non-toxic salt thereof wherein:
$R_5$ and $R_6$ are the same or different and represent hydrogen;
lower alkyl optionally substituted with halogen, —$OR_1$, —$NR_2R_3$, $SR_4$; or
lower alkyl optionally substituted with aryl or heteroaryl mono-, di- or trisubstituted independently with halogen, hydroxyl, lower alkyl, lower alkoxy, amino, thiol, or mono- or dialkylamino where each alkyl portion is lower alkyl;
$R_1$ is hydrogen, or lower alkyl or cycloalkyl optionally substituted independently with lower alkoxy or mono- or dialkylamino where each alkyl portion is lower alkyl;
$R_2$ and $R_3$ are the same or different and represent hydrogen, lower alkyl, cycloalkyl; or
$R_2$ and $R_3$ together with the nitrogen atom to which they are attached form a heterocyclic moiety;

R₄ is hydrogen, or lower alkyl or cycloalkyl optionally substituted independently with lower alkoxy or mono- or dialkylamino where each alkyl portion is lower alkyl; or R₅ and R₆ are the same or different and represent aryl or heteroaryl mono-, di- or trisubstituted independently with halogen, hydroxyl, lower alkyl, lower alkoxy, amino, thiol, or mono- or dialkylamino where each alkyl portion is lower alkyl; or R₅ and R6 together with the carbon atom to which they are attached form a 5, 6, or 7 membered carbocyclic ring.

6. A compound according to claim 1 of the Formula:

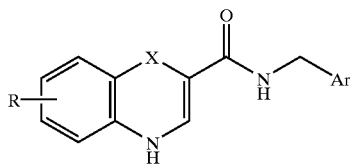

or the pharmaceutically acceptable non-toxic salts thereof wherein:

X is S=O, or O=S=O;

R represents up to 4 groups independently selected from hydrogen, halogen, hydroxy, amino, nitro, cyano, —SH, haloalkyl, lower alkyl, alkenyl, alkynyl, mono- or dialkylamino, or alkoxy; and Ar is phenyl or pyridyl, optionally mono-, di-, or trisubstituted with halogen, hydroxy, amine, haloalkyl, —SH, lower alkyl, alkenyl, alkynyl, alkoxy, or mono or dialkylamino.

7. A compound according to claim 1 which is N-2-thiazolylmethyl-1,1-dioxide-1,4-benzothiazine-2-carboxamide.

8. A compound according to claim 1 which is N-2-thiophenylmethyl-1,1-dioxide-1,4-benzothiazine-2-carboxamide.

9. A compound according to claim 1 which is N-benzyl-1,1-dioxide-1,4-benzothiazine-2-carboxamide.

10. A compound according to claim 1 which is N-2-methoxybenzyl-1-oxide-1,4-benzothiazine-2-carboxamide.

11. A compound according to claim 1 which is N-benzyl-1-oxide-1,4-benzothiazine-2-carboxamide.

12. A compound according to claim 1 which is N-3-methoxybenzyl-1-oxide-1,4-benzothiazine-2-carboxamide.

13. A compound according to claim 1 which is N-4-methoxybenzyl-1-oxide-1,4-benzothiazine-2-carboxamide.

14. A compound according to claim 1 which is N-2-ethoxybenzyl-1-oxide-1,4-benzothiazine-2-carboxamide.

15. A compound according to claim 1 which is N-3-ethoxybenzyl-1-oxide-1,4-benzothiazine-2-carboxamide.

16. A compound according to claim 1 which is N-4-ethoxybenzyl-1-oxide-1,4-benzothiazine-2-carboxamide.

17. A compound according to claim 1 which is N-2-chlorobenzyl-1-oxide-1,4-benzothiazine-2-carboxamide.

18. A compound according to claim 1 which is N-3-chlorobenzyl-1-oxide-1,4-benzothiazine-2-carboxamide.

19. A compound according to claim 1 which is N-4-chlorobenzyl-1-oxide-1,4-benzothiazine-2-carboxamide.

20. A compound according to claim 1 which is N-2-fluorobenzyl-1-oxide-1,4-benzothiazine 2-carboxamide.

21. A compound according to claim 1 which is N-3-fluorobenzyl-1-oxide-1,4-benzothiazine-2-carboxamide.

22. A compound according to claim 1 which is N-4-fluorobenzyl-1-oxide-1,4-benzothiazine-2-carboxamide.

23. A compound according to claim 1 which is N-methylbenzyl-1-oxide-1,4-benzothiazine-2-carboxamide.

24. A compound according to claim 1 which is N-α-methylbenzyl-1-oxide-1,4-benzothiazine-2-carboxamide.

25. A compound according to claim 1 which is N-3,4-methylenedioxybenzyl-1-oxide-1,4-benzothiazine-2-carboxamide.

26. A compound according to claim 1 which is N-3,4-dimethoxybenzyl-1-oxide-1,4-benzothiazine-2-carboxamide.

27. A compound according to claim 1 which is N-2-fluoro-4-methoxybenzyl-1-oxide-1,4-benzothiazine-2-carboxamide.

28. A compound according to claim 1 which is N-2-fluoro-4-propoxybenzyl-1-oxide-1,4-benzothiazine-2-carboxamide.

29. A compound according to claim 1 which is N-n-butyl-1-oxide-1,4-benzothiazine-2-carboxamide.

30. A compound according to claim 1 which is N-2-thiophenylmethyl-1-oxide-1,4-benzothiazine-2-carboxamide.

31. A compound according to claim 1 which is N-3-thiophenylmethyl-1-oxide-1,4-benzothiazine-2-carboxamide.

32. A compound according to claim 1 which is N-2-furanylmethyl-1-oxide-1,4-benzothiazine-2-carboxamide.

33. A compound according to claim 1 which is N-4-picolyl-1-oxide-1,4-benzothiazine-2-carboxamide.

34. A compound according to claim 1 which is N-2-chlorobenzyl-1,1-dioxide-1,4-benzothiazine-2-carboxamide.

35. A compound according to claim 1 which is N-3-chlorobenzyl-1,1-dioxide-1,4-benzothiazine-2-carboxamide.

36. A compound according to claim 1 which is N-2-bromobenzyl-1,1-dioxide-1,4-benzothiazine-2-carboxamide.

37. A compound according to claim 1 which is N-2-methoxybenzyl-1,1-dioxide-1,4-benzothiazine-2-carboxamide.

38. A compound according to claim 1 which is N-3,4-dimethoxybenzyl-1,1-dioxide-1,4-benzothiazine-2-carboxamide.

39. A compound according to claim 1 which is N-2,3-dimethoxybenzyl-1,1-dioxide-1,4-benzothiazine-2-carboxamide.

40. A compound according to claim 1 which is N-2-furanylmethyl-1,1-dioxide-1,4-benzothiazine-2-carboxamide.

41. A compound according to claim 1 which is N-3-dimethylaminomethylbenzyl-1,1-dioxide-1,4-benzothiazine-2-carboxamide.

42. A compound according to claim 1 which is N-4-methylaminomethylbenzyl-1,1-dioxide-1,4-benzothiazine-2-carboxamide.

43. A compound according to claim 1 which is N-4-imidazolymethylbenzyl-1,1-dioxide-1,4-benzothiazine-2-carboxamide.

44. A compound according to claim 1 which is N-3-ethoxypropyl-11--dioxide-1,4-benzothiazine-2-carboxamide.

45. A pharmaceutical composition comprising an effective amount of a compound according to claim 1 combined with at least one pharmaceutically acceptable carrier or excipient.

46. A method for the treatment of anxiety, depression, a sleep disorder, or cognitive impairment comprising administering to a patient in need of such treatment an effective amount of a compound according to claim 1.

* * * * *